(12) United States Patent
Stark et al.

(10) Patent No.: US 8,722,134 B2
(45) Date of Patent: May 13, 2014

(54) POST-HARVEST TREATMENT OF FRUITS WITH AN ANTIFUNGAL COMPOSITION

(75) Inventors: Jacobus Stark, Rotterdam (NL); Ferdinand Theodorus Jozef Van Rijn, Delft (NL); Jan Hendrik Hunik, The Hague (NL)

(73) Assignee: DSM IP Assets B.V., Heerlen (NL)

( * ) Notice: Subject to any disclaimer, the term of this patent is extended or adjusted under 35 U.S.C. 154(b) by 1016 days.

(21) Appl. No.: 12/518,176

(22) PCT Filed: Dec. 6, 2007

(86) PCT No.: PCT/EP2007/063420
§ 371 (c)(1),
(2), (4) Date: Oct. 19, 2009

(87) PCT Pub. No.: WO2008/068308
PCT Pub. Date: Jun. 12, 2008

(65) Prior Publication Data
US 2010/0050299 A1    Feb. 25, 2010

(30) Foreign Application Priority Data

Dec. 8, 2006 (EP) .................................. 06125673
Jul. 19, 2007 (EP) .................................. 07112772

(51) Int. Cl.
*A01G 5/06*    (2006.01)

(52) U.S. Cl.
USPC .......................................................... 427/4

(58) Field of Classification Search
USPC ....................................................... 800/298
See application file for complete search history.

(56) References Cited

U.S. PATENT DOCUMENTS

| | | | | |
|---|---|---|---|---|
| 4,139,616 A * | 2/1979 | Ducret et al. | ................. | 514/141 |
| 4,148,891 A | 4/1979 | Smink | | |
| 4,698,334 A * | 10/1987 | Horriere et al. | ............... | 514/141 |
| 4,806,445 A * | 2/1989 | Horriere et al. | ............... | 514/141 |
| 4,849,219 A * | 7/1989 | Staub et al. | .................... | 424/605 |
| 5,552,151 A | 9/1996 | Noordam et al. | | |
| 5,597,598 A | 1/1997 | Van Rijn et al. | | |
| 5,821,233 A * | 10/1998 | Van Rijn et al. | ................. | 514/31 |
| 5,962,510 A | 10/1999 | De Haan et al. | | |
| 6,150,143 A | 11/2000 | Raghoenath et al. | | |
| 6,655,081 B1 | 12/2003 | Stark et al. | | |
| 6,720,313 B1 * | 4/2004 | Maynard | ......................... | 514/75 |
| 7,816,332 B2 | 10/2010 | Stark et al. | | |
| RE42,394 E * | 5/2011 | Mudge | ........................... | 514/141 |
| 2011/0047654 A1 * | 2/2011 | Stark et al. | .................... | 800/298 |

FOREIGN PATENT DOCUMENTS

| | | |
|---|---|---|
| EP | 0290155 | 11/1988 |
| FR | 2 732 191 | 10/1996 |
| WO | WO 0101780 A1 * | 1/2001 |
| WO | WO 03053172 A1 * | 7/2003 |
| WO | 2005/074687 | 8/2005 |
| WO | WO 2006136551 A1 * | 12/2006 |

OTHER PUBLICATIONS

Meredith, Donald S. "Studies on *Gloeosporium musarum* Cke. and Massee causing storage trost of Jamaican bananas..." Ann Appl Biol 48(3) pp. 518-528 1960 Abstract.*
International Search Report for PCT/EP2007/063420, mailed Nov. 26, 2008.
International Preliminary Report on Patentability for PCT/EP2007/063420, mailed May 8, 2009.

* cited by examiner

*Primary Examiner* — Wendy C Haas
(74) *Attorney, Agent, or Firm* — Miles & Stockbridge, P.C.

(57) ABSTRACT

The present invention relates to the treatment of wounds occurring from cutting bananas and pineapples from a tree with a composition containing natamycin and at least one phosphite containing compound.

20 Claims, No Drawings

POST-HARVEST TREATMENT OF FRUITS WITH AN ANTIFUNGAL COMPOSITION

This application is the U.S. national phase of International Application No. PCT/EP2007/064320, filed 6 Dec. 2007, which designated the U.S. and claims priority to Europe Application No(s).06125673.1, filed 8 Dec. 2006 and 07112772.4, filed 19 Jul. 2007, the entire contents of each which are hereby incorporated by reference.

FIELD OF THE INVENTION

The present invention discloses a new antimicrobial composition to prevent post-harvest microbial spoilage of bananas and pineapples.

BACKGROUND OF THE INVENTION

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

In that respect bananas are an important crop. Bananas are ranked fourth after rice, wheat and maize in human consumption. The banana plant is an herb belonging to the genus *Musa* and is grown in more than hundred countries worldwide. Most of the bananas are consumed by the local population, but also great volumes are exported to e.g. the USA, Europe and Japan.

Both banana plants and banana fruits are sensitive for moulds after harvesting. Panama disease caused by *Fusarium oxysporum* is the most widely spread disease of banana plants. Also the moulds *Mycosphaerella fijiensis* and *Mycosphaerella musicola* cause diseases of banana leaves, the so-called Black and Yellow Sigatoka disease.

In WO 2005/074687 a new antifungal composition containing e.g. natamycin to prevent growth of these spoilage moulds on the banana plants in the field is described. The invention described in WO 2005/074687 offers a solution to protect banana plants in the field against pathogenic moulds.

FR 2 732 191 discloses a method for treating cercosporiose by applying an antifungal composition comprising a fosetyl-Al and optionally a triazole fungicide to the aerial parts of banana plants.

Besides mould growth on banana plants in the field, spoilage of bananas by moulds after harvesting is an issue of major concern. This so called "crown rot" is caused by mould infection after cutting the banana hand from the main stem. At this stage mould spores easily enter the wound via surface liquid and the latex-like sap from the injury. Later during transport and/or ripening the spores can germinate and the moulds grow further into the banana hand and will spoil the bananas. Crown rot can be caused by a number of fungal species. The most important species are *Fusarium pallidoroseum, Colletotrichum musae, Verticillium theobromae, Thielaviopsis paradoxa, Lasiodiplodia theobromae, Deightoniella torulosa* and *Fusarium roseum*. Crown rot leads to considerable losses of bananas grown for local consumption and of exported bananas.

To prevent mould damage, after harvesting at least all export bananas, but also many bananas for local consumption, receive a post-harvest treatment on the wound and close to the wound with an antifungal composition. Examples of fungicides applied in today's practice are thiazoles, thiabendazole, benomyl, imidazoles such as imazalil or mixtures thereof.

EP 0 290 155 discloses an absorbent sheet material for application to plant wounds comprising a flexible laminate of a sheet material, a permeable layer, absorbent material and a fungicide e.g. thiabendazole.

U.S. Pat. No. 4,148,891 discloses antifungal preparations of polyene antibiotics dissolved in a mixture of a lower alkanol and a lower alkanoic acid for preventing or inhibiting mould growth on agricultural products such as bananas.

Griffee and Pinegar (1974) examined several fungicides in the treatment of crown rot. Also pimaricin, now known as natamycin, was included in this study. From many other publications it is known that natamycin is a very effective antifungal compound. The authors indeed stated that natamycin showed a broad spectrum action. However, they also concluded that natamycin was not sufficiently active to give satisfactory control of moulds on bananas.

In spite of extensive treatment with the fungicides presently applied, spoilage problems still occur. It is known that moulds rather easily develop resistance to antifungal compounds, which is also the case for several moulds causing spoilage of bananas. When resistant strains develop, selection will take place and mould problems will increase, leading to the use of even higher amounts of fungicides. Further, many of the fungicides applied on bananas cause environmental pollution and human health problems. Also workers safety is an important issue, as it is known that all farm workers come in close contact with high concentrations of these harmful fungicides.

Pineapple belongs to the genus *Ananas*. It is the second fruit harvest of importance after bananas, contributing to over 20% of the world production of tropical fruits. A large part of the pineapples is consumed as fresh fruit in producing countries, but a considerable amount of pineapples is also exported. Pineapples have problems with respect to crown rot that are comparable with bananas. Also in the case of pineapples a wound vulnerable for moulds is present after harvesting. Moulds may infect the pineapple in a similar way as described for bananas leading to spoilage and economic losses.

Consequently, it can be concluded that there is a severe need for more effective, more environmental friendly, lower-toxicity and less harmful antimicrobial compounds/compositions, e.g. antifungal compounds/compositions, for the treatment of bananas, pineapples and comparable crops.

DESCRIPTION OF THE INVENTION

The present invention solves the problem by providing a new synergistic antimicrobial, e.g. antifungal, composition comprising a polyene antifungal agent and at least one phosphite containing compound and a process for the treatment of bananas, pineapples and other crops by applying the new composition to the fruits. By applying the new antimicrobial composition mould and/or fungal growth on or in bananas, pineapples and other crops can be prevented. In other words, the new compositions of the invention protect bananas, pineapples and other crops from mould and/or fungal growth and/or from mould and/or fungal infection and/or from fungal spoilage. The composition is advantageously applied on crops after harvesting, preferably crops that show a wound after harvesting. In other words, the harvesting of the crops results in a wound and the wound is treated with a composition according to the invention. In general, the wound occurs when the crop, e.g. fruit such as banana or pineapple, is removed from the plant it is grown on. For instance, bananas cut from a banana plant have a wound that is a consequence of the cutting. Cutting can be done with a knife, a chopper, a hatchet or the like. It can be done by hand or automatically. So, in general the harvested crop, which is preferably fruit, is connected to its plant by a stalk which will be broken by mechanical force.

Unexpectedly, the present inventors have found that the protection of e.g. bananas and pineapples after harvesting against moulds is markedly enhanced when a polyene fungicide, e.g. natamycin, is combined with a natural crop protection compound belonging to the group of phosphites, e.g. $KH_2PO_3$ or $K_2HPO_3$ or a mixture of both phosphite salts, and the combination is applied on wounds of the fruits. Phosphite containing compounds as used herein means compounds comprising a phosphite group, i.e. $PO_3$ (in the form of e.g. $H_2PO_3^-$, $HPO_3^{2-}$ or $PO_3^{3-}$) and includes compounds such as phosphorous acid and phosphonic acid as well as derivatives thereof such as esters and/or alkali metal or alkaline earth metal salts thereof.

The compositions of the present invention therefore comprise a polyene fungicide and at least one phosphite containing compound. In an embodiment the compositions of the invention comprise 0.1 g or less lignosulphonate, more preferably 0.1 g or less polyphenol, per gram polyene fungicide. Preferably, they comprise 0.01 g or less lignosulphonate, more preferably 0.01 g or less polyphenol, per gram polyene fungicide. In particular, they are free of lignosulphonate and preferably free of polyphenol.

Suitable examples of polyene fungicides applied in the compositions of the invention are natamycin, nystatin, amphotericin B, filipin and lucensomycin. The preferred polyene fungicide is natamycin. In an embodiment the compositions may also contain two or more different polyene fungicides. It is to be understood that derivatives of polyene fungicides including, but not limited to, salts or solvates of polyene fungicides or modified forms of polyene fungicides may also be applied in the compositions of the invention. An example of a commercial product containing natamycin is the product with the brand name Delvocid®. Delvocid® is produced by DSM Food Specialties (The Netherlands) and contains 50% (w/w) natamycin. Said commercial products can be incorporated in the compositions of the invention.

Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and ($C_1$-$C_4$) alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in the crop or plant are metabolized into phosphite compounds can also be included in the compositions of the present invention. Examples are phosphonates such as the fosetyl-aluminium complex. In e.g. a crop or plant the ethyl phosphonate part of this molecule is metabolized into a phosphite. An example of such a compound in the commercial ethyl hydrogen phosphonate product called Aliette® (Bayer, Germany).

Composition of the invention may have a pH of from 4 to 8, preferably of from 5 to 7. They may be solid, e.g. powder compositions, or may be liquid. Advantageously, they are liquids which can be applied by dipping, spraying or electrostatic spraying of e.g. bananas or pineapples. Alternatively, the wounds on the bananas or pineapples can also be treated using a paintbrush or e.g. a pad of cotton wool or cellulose pads impregnated with the antifungal compositions of the invention. The compositions of this invention can also be applied by using plaster-like carriers which are placed on the wound. Moreover, resin-like or wax-like compositions known in the art which cover the wound surface can be applied. In another aspect of this invention the antimicrobial compositions may be applied by means of a fruit coating. Examples of compounds applied as fruit coating are xanthan gum, sugars, glycerides and waxes such as beeswax.

For all these treatments methods and equipment well-known to a person skilled in the art can be used. A main advantage of the brush method, plaster-like compositions and spraying resins on the wound surface is that the fungicide is directly applied on the wound tissue and not on the whole fruit. On the other hand, aqueous dipping or spraying applications using automatic systems reduce the labour costs and are more cost-effective.

The compositions of the present invention are applied after harvesting. In the case of bananas preferably directly after the banana hands are cut from the stems. In case the bananas are washed, the compositions of the invention can be applied if the bananas come out of the wash tanks. Wash tanks are used to remove dust and field heat from the bananas. In case the bananas are put into specific de-latexing tanks to remove the latex which is leaking from the wound originating from the cutting of the hands and consequently preventing latex drips on the bananas that may form ugly spots, the compositions of the invention can be applied if the bananas come out of the de-latexing tanks. Alternatively, the compositions of the present invention may be added to the washing or de-latexing solutions themselves. Thereafter, the hands may be cut into clusters of four to six fingers (bananas) which are washed again. Also during or after this additional washing step the compositions of the invention can be applied. In an embodiment bananas or pineapples may also be treated with a composition comprising a polyene antifungal, e.g. natamycin, followed by treatment with a composition comprising at least one phosphite containing compound or vice versa. In addition, bananas can be treated with other antifungal and/or antimicrobial compositions either prior to or after treatment of the bananas with the compositions of the invention.

After treatment with the antimicrobial compositions of the invention the bananas may be packed in plastic, e.g. in the so-called mini wet-pack system commonly used for packaging of export bananas dip-treated in an antimicrobial composition. Alternatively, the bananas may be packed in boxes and shipped.

The compositions of the present invention also include concentrated stock suspensions/solutions and concentrated dry products such as e.g. powders, granulates and tablets. They can be used to prepare compositions for immersion or spraying of the bananas, pineapples or other crops.

A composition of the present invention will generally comprise 0.05 g/l to 100 g/l and preferably 0.1 g/l to 50 g/l of a polyene fungicide. Preferably, the amount is from 0.1 g/l to 3 g/l. Preferably, the polyene fungicide is natamycin. The composition will generally comprise 0.5 g/l to 1000 g/l and preferably 1 g/l to 500 g/l potassium phosphite. More preferably, the amount of potassium phosphite is from 2 g/l to 30 g/l. According to the present invention also other phosphites may be used in equimolar amounts to the potassium phosphite. In an embodiment the concentration of the phosphite, i.e. $PO_3$ group, in the composition of the invention is between 1 and 1000 mM, preferably between 10 and 750 mM and more preferably between 25 and 500 mM.

In addition, the compositions of the invention may also contain at least one other antifungal compounds such as e.g. imazalil (Janssen Pharmaceutica NV, Belgium), thiabendazole (e.g. the commercial product TECTO® Flowable SC of Syngenta, USA), benomyl, captan (nonsystemic phthalimide fungicide), prochloraz (N-propyl-N-[2-(2,4,6-trichlorophenoxy)ethyl] imidazole-1-carboxamide) and formalin and commercial products known under the name Topsin® M (Cerexagri Inc, active ingredient thiofanaat-methyl), Jet-5® (Certis Europe BV, The Netherlands, active ingredients peracetic acid and hydrogenperoxide) and Shirlan® (Syngenta, Switserland, active ingredient fluazinam). Further suitable antifungal compounds can be found in Gewasbeschermingsgids 2006, Gids voor gewasbescherming in de land-en tuinbouw en het openbaar en particulier green, Plantenziektenkundige Dienst, 2006, 560 pages, Paperback, Gewasbeschermingsgids—ISSN 1571-201X, Volume 18.

The composition of the invention may advantageously contain at least one sticking agent, which improves the sticking of the antifungal compound to the surface of e.g. the banana or pineapple fruits. Examples of such sticking agents are latex based products like Prolong® (Holland Fyto B.V., The Netherlands) and Bond® (Loveland Industries Ltd), pilonene/terpene based products like Nu-film® (Hygrotech Saad) and Spray-Fast® (Mandops) and long chain polysaccharides like xanthan gum, gellan gum and guar gum. Alternatively, the sticking agent may be a polymer or co-polymer from a type of polymer such as polyacrylate and polyethylene e.g. Neocryl® (DSM, The Netherlands). The composition of the invention may also comprise two or more different sticking agents.

For treating objects with a hydrophobic surface such as e.g. bananas or pineapples, the addition of at least one surfactant may be of advantage. The optional addition of said compounds to the compositions of the invention is therefore also included in this invention. Examples of useful surfactants are anionic tensides such as sodium lauryl sulphate or polyethylene alkyl ethers or polyoxyethylethers, e.g Tween® 60, 61 or 65. Other examples of useful surfactants are organo silicones, sulfosuccinates, alcohol ethoxylates, fatty acid ethoxylates, fatty acid propoxylates and the commercial product Zipper® (Asepta BV, The Netherlands). So, in a specific embodiment the compositions of the invention may further comprise additional compounds such as surfactants, sticking agents, suitable carriers and adjuvants ordinarily employed in formulation technology, including, but not limited to, mineral substances, solvents, dispersants, emulsifiers, wetting agents, stabilisers, antifoaming agents, buffering agents and antioxidants.

To improve the effectiveness and the practical use of the compositions of the present invention also compounds to combat insects, nematodes, mites and bacteria may be added to the antifungal composition. Examples of such compounds are Admire® (Bayer), formalin and Actellic® (Syngenta, Switserland).

Furthermore, the invention provides crops treated with a composition of the present invention. The treated crops may contain a coating comprising a composition of the invention. In an embodiment the treated crops comprise from 0.01 to 20 mg/dm$^2$, preferably from 0.1 to 10 mg/dm$^2$, natamycin on their surface. In a further embodiment they comprise from 0.1 to 600 mg/dm$^2$, preferably from 3 to 300 mg/dm$^2$ potassium phosphite on their surface. According to the present invention also other phosphite containing compounds may be used, therefore, the treated crops may comprise other phosphite containing compounds in equimolar amounts to the potassium phosphite on their surface. Examples of such crops are fruits such bananas, pineapples and other fruits having a wound when harvested. In case of bananas the compositions can be applied on banana stems, banana hands, banana clusters and even on single bananas. So, these banana "formats" treated with a composition of the present invention are also included in the present invention. In an embodiment only the wound resulting from harvesting of the fruit is treated with the compositions according to the invention. The wound may be present at the stalk of the banana, in which case only the stalk of the banana is treated with the compositions according to the invention.

EXAMPLES

Example 1

Treatment of Bananas

In this experiment organic bananas, Sabrosa® from the Dominican Republic, were used. The bananas were obtained from a local retailer in The Netherlands. The bananas were treated with spores of the phytopathogenic mould *Colletotridcum musae* CBS19231. The mould spores were obtained using well-known methods. The bananas were injured according to the method described by de Lapere de Bellaire and Dubois (1987). Bananas were wounded two times using a cork borer followed by contamination with approximately $2.5 \times 10^4$ mould spores of *C. musae* CBS19231 per wound. After incubation for 4 hours at room temperature, the bananas were dipped for one minute in one of the following compositions: a) no treatment (control 1), b) dipped in water (control 2), c) dipped in 1000 ppm natamycin, d) dipped in 240 mM of potassium phosphite, e) dipped in 1000 ppm of natamycin+ 240 mM of potassium phosphite. The experiment was executed in triplo; the natamycin and potassium phosphite solution were prepared using well-known methods. All compositions contained 0.1% (v/v) of the sticking agent Bond® (Loveland Industries Ltd.) and 0.14% (v/v) of the surfactant Zipper® (Asepta BV, The Netherlands). After this treatment the bananas were incubated in closed boxes at 21° C. at elevated humidity. Each day the bananas were judges visually on mould development.

After 15 days the 2 wounds on the 3 bananas of both controls (compositions a and b) were moulded (6 out of 6 wounds). Also the bananas treated with natamycin (composition c) and potassium phosphite (composition d) alone showed mould growth in all 6 and 5 out of 6 wounds, respectively. However, in the bananas treated with the composition comprising natamycin and phosphite (composition e) only in 2 out of 6 wounds mould growth was observed.

The results (see Table 1) clearly demonstrate that in a challenge test using high mould contaminations, a composition comprising natamycin and a phosphite compound protects bananas better against moulds than natamycin or phosphite alone. Surprisingly, the combined application of natamycin and phosphite leads to a strong synergistic reduction in infection.

Example 2

Treatment of Bananas

The experiment described in this example was done identically compared to the experiment described in Example 1, with the proviso that the wounds were made with a knife at the stalk of the bananas.

After 15 days of incubation in all wounds of both controls (compositions a and b) and in all wounds of the phosphite treated bananas (composition d) moulds developed. Mould growth was also observed on 2 of 3 bananas treated with natamycin alone (composition c). In the bananas treated with a composition comprising natamycin and phosphite (composition e) only on 1 banana mould growth was observed.

These results (see Table 2) clearly demonstrate that also in this challenge test using high mould contamination, the composition of the invention protects bananas much better against moulds than natamycin or phosphite alone.

Example 3

Treatment of Freshly Harvested Banana Clusters

In this experiment freshly harvested bananas were used. A few days after harvesting and the de-latexing treatment to remove latex which is leaking from the wounds using well-known methods, the bananas were infected with mould spores and treated as described in Example 1. For each composition, 3 clusters comprising 4 bananas per cluster were used (experiment done in triplo).

After 15 days of incubation on all bananas (12) of the clusters treated with control compositions (compositions a and b) and on all bananas of the clusters treated with natamycin alone (composition c) or phosphite alone (composition d) moulds were observed, while in only 3 of the 12 bananas of the clusters dipped in the composition comprising natamycin and phosphite (composition e) some mould growth was observed.

These results (see Table 3), obtained using freshly harvested bananas, clearly demonstrate that the compositions of the invention protect bananas effectively against moulds.

Example 4

Treatment of Freshly Harvested Bananas

The experiment described in this example was done identically compared to the experiment described in Example 3, with the proviso that bananas were harvested and thereafter new wounds were made with a knife at the stalk of the banana clusters (2 wounds were made per cluster).

After 15 days of incubation in all banana clusters treated with the controls (compositions a and b) and in all of the natamycin treated banana clusters (composition c) moulds developed. Severe mould growth was also observed on 2 of the 3 banana clusters treated with phosphite alone (composition d). On the banana clusters treated with a composition comprising natamycin and phosphite (composition e) only some minor mould growth was observed.

The results of this experiment (see Table 4) demonstrate that banana stalks are effectively protected by the compositions of the invention Example 5

Treatment of Bananas

The experiment described herein was executed as described in Example 1. However, in this experiment the sticking agent Bond® and the surfactant Zipper® were not used; instead Neocryl® (DSM) and xanthan were applied in a concentration of respectively 21.3 g/l and 1.0 g/l. In this experiment 12 wounds were made instead of 6 (2 wounds per banana; 6 bananas wounded).

After 15 days all wounds of the control bananas showed mould growth, 25% of the wounds of the bananas treated with phosphite were moulded and 50% of the wounds on natamycin treated bananas showed mould growth. On the bananas treated with the composition of the invention (natamycin and phosphite) no mould growth was observed after 15 days of incubation.

These results (see Table 5) clearly demonstrate that although the degree of mould contamination in this experiment was extremely high and the incubation conditions were optimal for fungal growth, the composition of the invention protected the bananas against moulding for at least 15 days.

Example 6

Treatment of Bananas

The experiment described herein was executed as described in Example 4, with the proviso that the sticking agent Bond® and the surfactant Zipper® were replaced by Neocryl® (DSM) and xanthan in a concentration of respectively 21.3 g/l and 1.0 g/l. Three clusters comprising 4 bananas each were wounded two times at the hand of the cluster resulting in a total number of wounds of 6.

After 15 days of incubation in all wounds of the two control banana groups moulds were growing. Also all wounds of clusters treated with natamycin or phosphite alone were moulded. However, on the clusters treated with the composition comprising natamycin and phosphite mould growth was observed in only 1 wound (see Table 6).

The results presented herein demonstrate that the compositions of the present invention can protect crops, e.g. fruits such as bananas and pineapples, from mould growth and further demonstrate that the compositions of the present invention show a synergistically enhanced activity compared to the activity of the active compounds when applied individually.

TABLE 1

Mould growth in wounds of bananas.

| Composition | Number of wounds showing mould growth/ Total number of wounds* |
|---|---|
| Composition a (control 1) | 6/6 |
| Composition b (control 2) | 6/6 |
| Composition c (natamycin) | 6/6 |
| Composition d (phosphite) | 5/6 |
| Composition e (natamycin + phosphite) | 2/6 |

*total number of wounds is 6 (3 bananas with 2 wounds per banana)

TABLE 2

Mould growth in wounds of bananas.

| Composition | Number of wounds showing mould growth/ Total number of wounds* |
|---|---|
| Composition a (control 1) | 3/3 |
| Composition b (control 2) | 3/3 |
| Composition c (natamycin) | 2/3 |
| Composition d (phosphite) | 3/3 |
| Composition e (natamycin + phosphite) | 1/3 |

*total number of wounds is 3 (3 bananas with 1 wound made at the stalk per banana)

TABLE 3

Mould growth on bananas in clusters.

| Composition | Number of bananas showing mould growth/ Total number of bananas* |
|---|---|
| Composition a (control 1) | 12/12 |
| Composition b (control 2) | 12/12 |
| Composition c (natamycin) | 12/12 |
| Composition d (phosphite) | 12/12 |
| Composition e (natamycin + phosphite) | 3/12 |

*total number of bananas is 12 (3 clusters with 4 bananas per cluster)

TABLE 4

Severe mould growth in wounds of bananas in clusters.

| Composition | Number of clusters showing severe mould growth/ Total number of clusters* |
|---|---|
| Composition a (control 1) | 3/3 |
| Composition b (control 2) | 3/3 |
| Composition c (natamycin) | 3/3 |
| Composition d (phosphite) | 2/3 |
| Composition e (natamycin + phosphite) | 0/3 |

*total number of clusters is 3

TABLE 5

Mould growth in wounds of bananas.

| Composition | Number of wounds showing mould growth/ Total number of wounds* |
|---|---|
| Composition a (control 1) | 12/12 |
| Composition b (control 2) | 12/12 |
| Composition c (natamycin) | 6/12 |
| Composition d (phosphite) | 3/12 |
| Composition e (natamycin + phosphite) | 0/12 |

*total number of wounds is 12 (6 bananas with 2 wounds per banana)

TABLE 6

Mould growth in wounds of bananas in clusters.

| Composition | Number of wounds showing mould growth/ Total number of wounds* |
|---|---|
| Composition a (control 1) | 6/6 |
| Composition b (control 2) | 6/6 |
| Composition c (natamycin) | 6/6 |
| Composition d (phosphite) | 6/6 |
| Composition e (natamycin + phosphite) | 1/6 |

*total number of wounds is 6 (3 clusters with 4 bananas per cluster with 2 wounds made per cluster at the hand of the cluster)

REFERENCES

Griffee P J and Pinegar J A (1974), Fungicides for control of the banana crown rot complex: in vivo and in vitro studies. Trop. Sci. 16, 3:107-120.

Lapeyre de Bellaire de L and Dubois C (1987), Distribution of Thiabendazole-Resistant *Colletotrichum musae* Isolates from Guadeloupe Banana Plantations. Plant disease 81:1378-1383.

The invention claimed is:

1. Process for the treatment of fruit selected from the group consisting of bananas and pineapples, the process comprising the step of applying a composition comprising a polyene antifungal agent and at least one phosphite containing compound to the fruit, wherein the polyene antifungal agent is natamycin, and wherein the fruit is treated after harvesting.

2. A process according to claim 1, wherein a wound resulting from harvesting of the fruit is treated.

3. A process according to claim 2, wherein the wound results from removing the fruit from a plant.

4. A process according to claim 1, wherein the composition is applied during or after washing of the fruit.

5. A process according to claim 1, wherein the composition further comprises at least one additional compound selected from the group consisting of a sticking agent, a surfactant, a further antifungal compound, a compound to combat insects, nematodes, mites and/or bacteria, a mineral substance, a solvent, a dispersant, an emulsifier, a wetting agent, a stabiliser, an antifoaming agent, a buffering agent and an antioxidant.

6. A fruit selected from the group consisting of bananas and pineapples treated with a composition comprising natamycin and at least one phosphite containing compound.

7. A fruit according to claim 6, wherein a wound resulting from harvesting of the fruit is treated with the composition and the composition is synergistic.

8. A fruit according to claim 6, wherein the composition further comprises at least one additional compound selected from the group consisting of a sticking agent, a surfactant, a further antifungal compound, a compound to combat insects, nematodes, mites and/or bacteria, a mineral substance, a solvent, a dispersant, an emulsifier, a wetting agent, a stabiliser, an antifoaming agent, a buffering agent and an antioxidant.

9. A process according to claim 1, wherein the composition has a synergistic effect.

10. A process according to claim 1, wherein the fruit comprises pineapples.

11. A process according to claim 1, wherein the fruit comprises bananas.

12. A process according to claim 1, wherein the phosphite containing compound comprises a potassium phosphite.

13. A process according to claim 1, wherein the composition consists essentially of at least one phosphite containing compound and natamycin.

14. A process according to claim 1, wherein the concentration of natamycin in the composition is between 0.05-100 g/L.

15. A process according to claim 1, wherein the concentration of natamycin in the composition is between 0.1-50 g/L.

16. A process according to claim 1, wherein the concentration of the phosphite containing compound is between 10-750mM.

17. A process according to claim 1, wherein the concentration of the phosphite containing compound is between 25-500mM.

18. A process according to claim 12, wherein the concentration of the potassium phosphite is between 25-500mM.

19. A process according to claim 1, wherein the concentration of natamycin is between 0.1-50 g/L and the concentration of the phosphite containing compound is between 25-500mM.

20. A process according to claim 1, wherein the concentration of natamycin is between 0.1-3 g/L and the concentration of the phosphite containing compound is between 50-300mM.

* * * * *